(12) United States Patent
Kiesele et al.

(10) Patent No.: US 6,584,827 B2
(45) Date of Patent: Jul. 1, 2003

(54) ELECTROCHEMICAL GAS SENSOR WITH DIAMOND ELECTRODE

(75) Inventors: Herbert Kiesele, Lübeck (DE); Frank Mett, Lübeck (DE); Peter Tschuncky, Lübeck (DE)

(73) Assignee: Drägerwerk Aktiengesellschaft (DE)

( * ) Notice: Subject to any disclaimer, the term of this patent is extended or adjusted under 35 U.S.C. 154(b) by 0 days.

(21) Appl. No.: 10/146,737

(22) Filed: May 16, 2002

(65) Prior Publication Data
US 2003/0046980 A1 Mar. 13, 2003

(30) Foreign Application Priority Data
Sep. 12, 2001 (DE) .......................................... 101 44 862

(51) Int. Cl.[7] ...................... G01N 27/40; G01N 27/413; G01N 27/30; H01L 27/14
(52) U.S. Cl. ...................... 73/31.05; 73/23.2; 204/280; 204/432; 205/794.5
(58) Field of Search .............................. 73/31.05, 23.2, 73/31.06, 23.31; 204/228.6, 426, 432, 280, 232; 422/94; 205/794.5

(56) References Cited

U.S. PATENT DOCUMENTS

| | | | | |
|---|---|---|---|---|
| 5,041,195 A | * | 8/1991 | Taylor et al. | 204/96 |
| 5,133,842 A | * | 7/1992 | Taylor et al. | 204/98 |
| 5,571,944 A | * | 11/1996 | Pfeifer et al. | 73/24.04 |
| 5,605,612 A | * | 2/1997 | Park et al. | 204/429 |
| 5,624,641 A | * | 4/1997 | Capetanopoulous et al. | 422/98 |
| 5,777,372 A | * | 7/1998 | Kobashi | 257/414 |
| 5,900,127 A | * | 5/1999 | Iida et al. | 204/290 F |
| 6,344,658 B1 | * | 2/2002 | Nakagawa et al. | 257/6 |
| 6,375,827 B1 | * | 4/2002 | Kurosu et al. | 205/687 |
| 6,423,193 B1 | * | 7/2002 | Miller et al. | 204/242 |

FOREIGN PATENT DOCUMENTS

DE 199 39 011 C1 1/2001

OTHER PUBLICATIONS

Yu V. Pleskov, Jan. 2000, Synthetic Diamond, a New Electrode Material for Electroanalysis, *Journal of Analytical Chemical*, vol. 55, No. 11, 2000, pp1045–1050.

* cited by examiner

Primary Examiner—Helen Kwok
Assistant Examiner—David John Wiggins
(74) Attorney, Agent, or Firm—McGlew and Tuttle, P.C.

(57) ABSTRACT

An electrochemical gas sensor for detecting a specific gas being measured with a plurality of electrodes (21, 3, 4), an electrolyte (7) and a gas-permeable membrane (9) has a reduced cross sensitivity with respect to interfering gases, a short response time and high sensitivity for the measured gas without the service life being reduced. The measuring electrode is a layer of doped diamond thin (21) on a porous substrate (22), where the gas-permeable memebrane is disposed over the measuring electrode to permit passage therethru of the gas being measured.

21 Claims, 1 Drawing Sheet

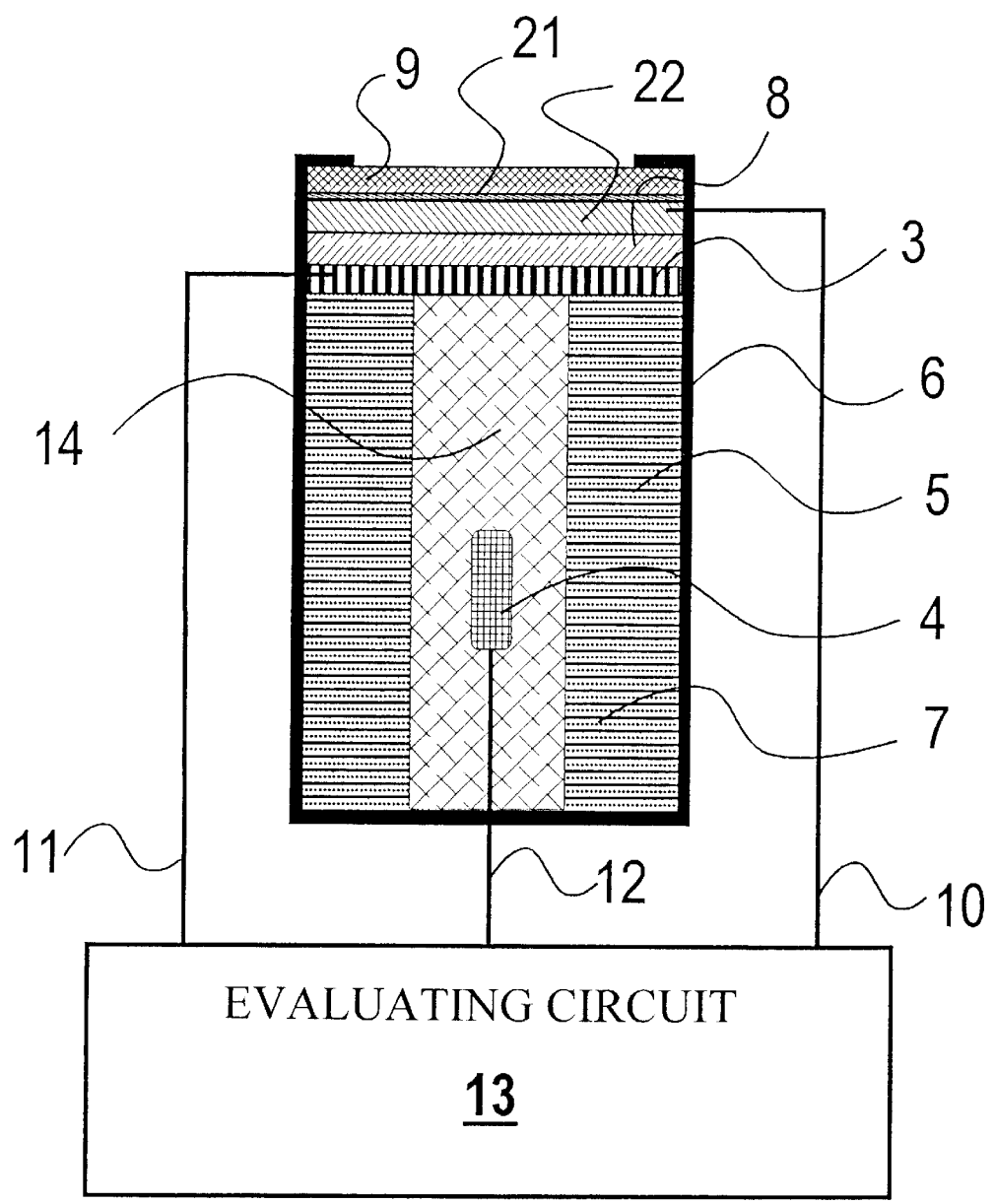

ELECTROCHEMICAL GAS SENSOR WITH DIAMOND ELECTRODE

FIELD OF THE INVENTION

The present invention pertains to an electrochemical gas sensor and more particularly to an electrochemical gas sensor with a plurality of electrodes, with an electrolyte and with a gas-permeable membrane.

BACKGROUND OF THE INVENTION

Such a gas sensor is shown in DE 199 39 011 C1, where the measuring electrode consists of diamond-like carbon (DLC). In this prior-art electrode, the diamond-like carbon is preferably applied to the gas-permeable membrane by a sputtering process in a radio frequency magnetron sputtering unit. This prior-art arrangement is very well suited for many applications, but the chemical stability it ensures and the potential window that can be reached are not sufficient for all measurement applications.

SUMMARY OF THE INVENTION

The object of the present invention is to propose an improved gas sensor of the type mentioned in the introduction, which has a reduced cross sensitivity with respect to interfering gases, has a short response time and high sensitivity for the measured gas without the service life being reduced. The measured gas may occur either in a mixture with other gases or even dissolved in a liquid, especially water.

According to the invention, an electrochemical gas sensor with a plurality of electrodes is provided. The sensor has an electrolyte and a gas-permeable membrane. At least the measuring electrode comprises a thin layer made of doped diamond on a porous substrate.

The thin layer may consist of the diamond doped with boron, especially with a doping corresponding to $10^{19}$ to $10^{21}$ boron atoms per cubic centimeter. The thin layer may also consist of the diamond doped with nitrogen. The doping particularly corresponds to about $10^{20}$ nitrogen atoms per cubic centimeter.

The thickness of the thin layer consisting of the doped diamond is advantageously 0.5 $\mu$m to 5 $\mu$m.

The thin layer consisting of the doped diamond may be advantageously prepared by deposition from the gaseous phase (CVD, Chemical Vapor Deposition). The porous substrate may be a quartz nonwoven. The layer thickness may be advantageously 0.2 $\mu$m to 0.5 $\mu$m. The quartz nonwoven may have a surface coating. This is preferably a silicon carbide or silicon nitride coating.

The surface of the thin layer consisting of the doped diamond is additionally doped with a precious metal, especially with gold, platinum and/or iridium. The auxiliary electrode may be designed as a thin layer consisting of the doped diamond on a porous substrate.

The essence of the present invention, that at least the measuring electrode is designed as a thin layer consisting of diamond doped with boron or nitrogen on a porous substrate has many advantages. The porous substrate preferably consists of the nonwoven material made of chemically pure quartz. The extent of the doping determines the optimal ranges for good, desirable electrical conductivity.

The preferred process for producing the diamond layer, by deposition from the gaseous phase (CVD, Chemical Vapor Deposition), is known per se from the publication "Synthetic Diamond, a New Electrode Material for Electroanalysis," Yu. V. Pleskov, *Journal of Analytical Chemistry*, Vol. 55, No. 11, 2000, pp. 1045 to 1050 and the references cited therein. In the diamond electrodes known currently, the diamond layers are applied either to a closed, planar substrate or to a metal grid or network.

According to the present invention, the thin diamond layer is applied according to the prior-art CVD process to a porous substrate, especially a quartz nonwoven. As a result, it is possible to produce the microporous electrode structures necessary for electrochemical gas sensors with a pore size of 0.1 $\mu$m to 100 $\mu$m, which is permeable to the electrolyte and the gas to be measured. Another advantage of the electrode structure thus prepared with the porous substrate is the good mechanical flexibility, which prevents the undesired formation of electrolyte gaps for the diffusion membrane.

The following essential advantages are observed in the case of gas sensors according to the present invention:

Extremely low residual currents are measured, so that even very low concentration ranges can be measured, low catalytic activity is observed, i.e., the reactions taking place at the electrode because of interfering gases, e.g., hydrogen sulfide ($H_2S$), are strongly inhibited, high long-term stability of the measured signal is obtained, a wide potential window is obtained, so that a wider range of measurement can be covered with respect to different measured gases, the double-layer capacity is low, and it also undergoes hardly any changes under temperature and moisture effects.

The widened potential window and the markedly improved chemical stability also make possible the conversion of highly chlorinated hydrocarbons, which do not react at conventional measuring electrodes of electrochemical gas sensors.

To specifically modify the catalytic properties, the surface of the electrodes according to the present invention may be doped with a precious metal. The surface of the porous substrate, especially the quartz nonwoven, can be chemically modified by applying a silicon carbide or silicon nitride layer.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only drawing is a schematic sectional view through an electrochemical gas sensor, which is especially suitable for measuring chlorine gas. The dimensions used are not true to scale and are shown, in general, in an enlarged form for illustration.

DESCRIPTION OF THE PREFERRED EMBODIMENTS

Referring to the drawing in particular, the electrochemical gas sensor according to the invention comprises a housing 6 defining an electrolyte space 5. The housing 6 is closed by a gas-permeable PTFE (polytetrafluoroethylene) membrane 9 with an electrolyte film. An electrolyte 7 is provided in the electrolyte space 5. A thin layer of boron-doped diamond 21 is connected to a porous substrate 22 to form a measuring electrode. An auxiliary electrode 3 made of silver or nickel plate is provided on a nonwoven material 8. A porous glass body 14 is provided in the electrolyte space 5. A reference electrode 4 is located behind the measuring electrode 21/22 and the auxiliary electrode 3. The contact wires 10, 11, 12 lead from the electrolyte space 5 through the housing 6 to the evaluating circuit 13 with a potentiostat contained therein.

The measured gas to be detected, e.g., chlorine, diffuses through the gas-permeable PTFE (polytetrafluoroethylene) membrane 9 and via the electrolyte film, which is extremely thin and is therefore not shown. The gas then reaches the measuring electrode, which is designed as a porous, thin layer made of diamond 21. The thin layer of diamond 21 is doped with boron and has a thickness is 0.7 $\mu$m. The thin layer of boron-doped diamond 21 is firmly connected to the porous substrate 22. The porous substrate 22 is a nonwoven material made of chemically pure quartz with a layer thickness of 0.3 mm. The quartz nonwoven is impregnated with the electrolyte 7, e.g., an aqueous lithium bromide. Another nonwoven 8, which is impregnated with electrolyte and consists of glass, quartz or a polymer, is located behind the porous substrate 22. The auxiliary electrode 3 made of silver or nickel plate is pressed onto the nonwoven 8 by means of a porous glass body 14. The reference electrode 4 is located protected behind the measuring electrode and the auxiliary electrode 3. The contact wires 10, 11, 12 lead from the electrolyte space 5 through the housing 6 to the evaluating circuit 13 with a potentiostat contained therein.

The auxiliary electrode 3 may also be designed as a thin layer of doped diamond on a porous substrate.

Doped diamond electrodes in electrochemical gas sensors offer the following advantages over the state of the art:
  Due to the excellent chemical stability and the mechanical stability, there is a long service life;
  the smooth and resistant surface prevents the so-called "electrode fouling" (coating of the surface), which may lead to complete blockage of the electrodes;
  the unusually low residual currents, which hardly increase even in case of changes in the temperature and moisture, make possible the determination of much lower gas concentrations;
  the extremely wide potential window and the formation of the highly reactive OH radicals make it possible to determine analytes that were not hitherto directly accessible to determination, e.g., highly chlorinated hydrocarbons.

While specific embodiments of the invention have been shown and described in detail to illustrate the application of the principles of the invention, it will be understood that the invention may be embodied otherwise without departing from such principles.

What is claimed is:

1. An electrochemical gas sensor, comprising:
   a plurality of electrodes including a measuring electrode for detecting a specific gas being measured, at least the measuring electrode being designed as a thin layer made of doped diamond on a porous substrate;
   an electrolyte; and
   a gas-permeable membrane disposed over the measuring electrode to permit passage therethru of the gas being measured.

2. An electrochemical gas sensor in accordance with claim 1, wherein said thin layer of diamond is doped with boron, with a doping corresponding to $10^{19}$ to $10^{21}$ boron atoms per cubic centimeter.

3. An electrochemical gas sensor in accordance with claim 1, wherein the thickness of said thin layer of doped diamond is 0.5 $\mu$m to 5 $\mu$m.

4. An electrochemical gas sensor in accordance with claim 1, wherein said thin layer of doped diamond is prepared by deposition from a gaseous phase chemical vapor deposition.

5. An electrochemical gas sensor in accordance with claim 1, wherein the plurality of electrodes include an auxiliary electrode designed as a thin layer of doped diamond on a porous substrate.

6. An electrochemical gas sensor for detecting a specific gas being measured, comprising:
   a sensor housing with an opening;
   an electrolyte in the housing;
   a gas-permeable membrane closing the opening
   a plurality of electrodes including a measuring electrode and an auxiliary electrode, at least the measuring electrode being designed as a thin layer made of doped diamond on a porous substrate, where the gas-permeable membrane is disposed over the measuring electrode to permit passage therethru of the gas being measured.

7. An electrochemical gas sensor in accordance with claim 6, wherein said thin layer of diamond is doped with boron, with a doping corresponding to $10^{19}$ to $10^{21}$ boron atoms per cubic centimeter.

8. An electrochemical gas sensor in accordance with claim 6, wherein said thin layer of diamond is doped with nitrogen, with a doping corresponding to about $10^{20}$ nitrogen atoms per cubic centimeter.

9. An electrochemical gas sensor in accordance with claim 6, wherein the thickness of said thin layer of doped diamond is 0.5 $\mu$m to 5 $\mu$m.

10. An electrochemical gas sensor in accordance with claim 6, wherein said thin layer of doped diamond is prepared by deposition from a gaseous phase chemical vapor deposition.

11. An electrochemical gas sensor in accordance with claim 6, wherein said porous substrate is a quartz nonwoven with a layer thickness of 0.2 mm to 0.5 mm.

12. An electrochemical gas sensor in accordance with claim 7, wherein the surface of said thin layer of doped diamond is additionally doped with a precious metal, especially with gold, platinum and/or iridium.

13. An electrochemical gas sensor in accordance with claim 6, wherein the plurality of electrodes include an auxiliary electrode designed as a thin layer of doped diamond on a porous substrate.

14. An electrochemical gas sensor in accordance with claim 6, further comprising:
   an evaluating circuit connected to said electrodes, said evaluating circuit including a potentiostat.

15. An electrochemical gas sensor in accordance with claim 6, further comprising:
   an evaluating circuit connected to said electrodes for determining gas characteristics from an electrochemical reaction occurring at said electrodes.

16. An electrochemical gas sensor, comprising:
   a plurality of electrodes including a measuring electrode for detecting a specific gas being measured, at least the measuring electrode being designed as a thin layer made of doped diamond on a porous substrate, said thin layer of diamond being doped with nitrogen, with a doping corresponding to about $10^{20}$ nitrogen atoms per cubic centimeter;

an electrolyte; and a gas-permeable membrane, where the gas-permeable membrane is disposed over the measuring electrode to permit passage therethru of the gas being measured.

17. An electrochemical gas sensor in accordance with claim 3, wherein the surface of the thin layer of doped diamond is additionally doped with a precious metal, especially with gold, platinum and/or iridium.

18. An electrochemical gas sensor, comprising:

a plurality of electrodes including a measuring electrode for detecting a specific gas being measured at least the measuring electrode being designed as a thin layer made of doped diamond on a porous substrate, said porous substrate being nonwoven quartz with a layer thickness of 0.2 mm to 0.5 mm;

an electrolyte; and a gas-permeable membrane, where the gas-permeable membrane is disposed over the measuring electrode to permit passage therethru of the gas being measured.

19. An electrochemical gas sensor in accordance with claim 1, wherein said quartz nonwoven has a surface coating of silicon carbide or silicon nitride.

20. An electrochemical gas sensor, comprising:

a plurality of electrodes including a measuring electrode for detecting a specific gas being measured, at least the measuring electrode being designed as a thin layer made of doped diamond on a porous substrate, said thin layer of diamond being doped with boron, with a doping corresponding to $10^{19}$ to $10^{21}$ boron atoms per cubic centimeter, a surface of said thin layer of doped diamond being additionally doped with a precious metal;

an electrolyte; and a gas-permeable membrane, where the gas-permeable membrane is disposed over the measuring electrode to permit passage therethru of the gas being measured.

21. A sensor in accordance with claim 20, wherein:

said precious metal is one of gold, platinum and/or iridium.

* * * * *